United States Patent [19]

Kroenke

[11] 4,406,840

[45] Sep. 27, 1983

[54] TRI(TRIDECYL)AMMONIUM MOLYBDATES

[75] Inventor: William J. Kroenke, Brecksville, Ohio

[73] Assignee: The B. F. Goodrich Company, Akron, Ohio

[21] Appl. No.: 402,484

[22] Filed: Jul. 28, 1982

[51] Int. Cl.³ .............................................. C07F 11/00
[52] U.S. Cl. ................................................. 260/429 R
[58] Field of Search ..................................... 260/429 R

[56] References Cited

U.S. PATENT DOCUMENTS

| | | | |
|---|---|---|---|
| 3,223,625 | 12/1965 | Cyphers et al. | 260/429 R X |
| 3,290,245 | 12/1966 | Elliott et al. | 260/429 R X |
| 3,349,108 | 10/1967 | Marzluff | 260/429 R |
| 4,053,455 | 10/1977 | Kroenke | 260/429 R |
| 4,153,792 | 5/1979 | Kroenke | 260/429 R X |
| 4,217,292 | 8/1980 | Kroenke | 260/429 R |
| 4,234,474 | 11/1980 | Kroenke | 260/429 R X |
| 4,235,770 | 11/1980 | Kroenke | 260/429 R X |
| 4,247,451 | 1/1981 | Kroenke | 260/429 R X |
| 4,248,766 | 2/1981 | Kroenke | 260/429 R X |
| 4,248,767 | 2/1981 | Kroenke | 260/429 R X |

*Primary Examiner*—Helen M. S. Sneed
*Attorney, Agent, or Firm*—James R. Lindsay

[57] ABSTRACT

Tri(tridecyl)ammonium molybdates having the empirical formula

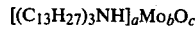

$$[(C_{13}H_{27})_3NH]_a Mo_b O_c$$

where a, b and c are (2,6,19); (4,8,26) or (6,7,24) are disclosed as novel amine molybdates which are useful as smoke retardant additives for vinyl chloride polymer compositions.

4 Claims, No Drawings

TRI(TRIDECYL)AMMONIUM MOLYBDATES

BACKGROUND OF THE INVENTION

Amine molybdates may be produced by reacting an amine or an amine salt with a molybdenum compound such as molybdenum trioxide ($MoO_3$), molybdic acid or a molybdenum salt in an acidic aqueous medium made acidic through the addition of a suitable acid such as an inorganic acid (exemplified by hydrochloric acid, nitric acid or sulfuric acid) or an organic acid containing 1 to 12 carbon atoms (exemplified by acetic acid, propionic acid, benzoic acid, and the like). The acidic mixture is refluxed, preferably while being stirred continuously, until the reaction is complete, usually for about ¼ to 4 hours.

Amine molybdates also may be produced, as described in U.S. Pat. No. 4,217,292, by reacting essentially stoichiometric quantities of molybdenum trioxide with an amine or an amine salt in an aqueous medium essentially free of acid and in which a water-soluble ammonium or monovalent metal or divalent metal or trivalent rare earth metal salt of an inorganic or organic acid is dissolved. Sometimes the reaction is carried out in a polar organic solvent instead of water.

The particular amine molybdate formed may depend upon which process is used to form the amine molybdate and the quantity of reactants present in the reaction mixture, as well as the reaction conditions.

SUMMARY OF THE INVENTION

The present invention pertains to a class of novel molybdates, namely, tri(tridecyl)ammonium molybdates, which may be represented by the formula:

$$[(C_{13}H_{27})_3NH]_a Mo_bO_c$$

where a, b and c are (2,6,19); (4,8,26) or (6,7,24). Like many other amine molybdates, the tri(tridecyl)ammonium molybdates function as effective smoke retardant additives for vinyl chloride polymers.

DETAILED DESCRIPTION OF THE INVENTION

Tri(tridecyl)ammonium molybdates may be produced by reacting ammonium dimolybdate [$(NH_4)_2Mo_2O_7$] and tri(tridecyl) amine [$(C_{13}H_{27})_3N$] in an acidic aqueous medium. Suitable acids include inorganic acids, such as hydrochloric acid, nitric acid, sulfuric acid, and the like, or mixtures thereof. The amount of acid used may be varied widely from about ½ to 10 or more molar equivalents of acid per molar equivalent of ammonium dimolybdate. However, about a 1/1 molar equivalent ratio is preferred. Sufficient water is included in the reaction mixture to insure a reaction medium that has a consistency that enables it to be easily stirred. Since tri(tridecyl)amine and the tri(tridecyl)ammonium molybdates of the present invention are insoluble in an aqueous medium, preferably, the ammonium dimolybdate is dissolved in the aforementioned aqueous medium while the tri(tridecyl)amine is dissolved in an organic solvent that is a solvent both for the tri(tridecyl)amine of the reaction mixture and for the amine molybdate reaction product and that is immiscible in water (benzene, toluene, methylene chloride or cyclohexane, for example). The two immiscible solutions are mixed together and heated to reflux while being stirred. The reaction materials are refluxed while being stirred continuously for about 0.25 to 16 hours. The tri(tridecyl)ammonium molybdate reaction product remains dissolved in the organic solvent phase of the mixture. After the reaction is completed, the two immiscible factions are separated from each other. The organic solvent phase, containing the tri(tridecyl)ammonium molybdate, is washed with water and dried over an appropriate desiccant, such as calcium hydride. If desired, the organic solvent can be removed from the tri(tridecyl)ammonium molybdate by evaporation or distillation. The molar ratio of ammonium dimolybdate to tri(tridecyl)amine will influence the tri(tridecyl)ammonium molybdates formed as a result of the reaction. Theoretical molybdenum/tri(tridecyl)amine molar ratios from 0.5/1 to 3/1 are used. However, the actual molar ratios that can be used in the reaction can be outside the stated range, but generally will produce mixtures of the molybdates. The tri(tridecyl)ammonium molybdates within the scope of the present invention are tri(tridecyl)ammonium hexamolybdate [$(C_{13}H_{27})_3NH]_2Mo_6O_{19}$, tri(tridecyl)ammonium heptamolybdate [$(C_{13}H_{27})_3NH]_6Mo_7O_{24}$ and tri(tridecyl)ammonium octamolybdate [$(C_{13}H_{27})_3NH]_4Mo_8O_{26}$.

The following examples more fully illustrate the preparation of the novel tri(tridecyl)ammonium molybdates of the present invention.

EXAMPLE I 5.00 grams of tri(tridecyl)amine were added to a 500 milliliter round-bottom flask equipped with a water-cooled condenser and a mechanical stirrer. 50 milliliters of methanol then were added to the flask, followed by the addition (in the order stated) of 4.47 grams of ammonium dimolybdate, 25 additional milliliters of methanol, 2.59 grams of a 37 percent hydrochloric acid solution mixed into 25 milliliters of methanol, and a final addition of 25 milliliters of methanol. The cloudy mixture in the flask was heated to reflux and refluxed while being stirred continuously for ½ hour. As the mixture was heated, it became light green in color, changed to yellow, then yellow-green, and finally to green. The contents of the flask were cooled to room temperature (about 25° C.). The methanol phase (which contained a sticky green mass) then was separated from the aqueous phase, poured through a coarse filter paper and collected in an erlenmeyer flask, the sticky green mass settling to the bottom of the erlenmeyer flask. The methanol was decanted off and the green mass was washed 3 times with methanol, decanting off the methanol wash after each washing. The green product was dried in a vacuum oven at 40° C. for 1 hour. The reaction product then was added to 45 milliliters of methylene chloride. The green sticky mass in the reaction product dissolved in the methylene chloride. The solution was filtered through a medium filter paper, the green liquid filtrate being collected in an erlenmeyer flask. Infrared analysis identified the green sticky mass to be tri(tridecyl) ammonium hexamolybdate.

EXAMPLE II 6.00 grams of tri(tridecyl)amine were dissolved in 80 milliliters of methylene chloride and added to a 1000 milliliter round-bottom flask equipped with a water-cooled condenser and a mechanical stirrer. 126 additional milliliters of methylene chloride were added to the flask. 3.58 grams of ammonium dimolybdate were dissolved in 160 milliliters of water. 2.07 grams of 37 percent hydrochloric acid were added to 20 milliliters of water. The aqueous hydrochloric acid solution was combined with the ammonium dimolybdate solution. The combined aqueous solutions were added to the round-bottom flask. 26 milliliters of additional water were added to the flask. The mixture in the flask was heated to reflux and refluxed while being stirred continuously for one hour. As the mixture was heated, the cloudy white mixture changed to light green in color. The contents in the flask were cooled to room temperature (about 25° C.) and added to a separatory funnel and the two immiscible phases were separated, one phase being an aqueous phase and the other being the methylene chloride phase. The methylene chloride phase was washed three times with water, separating the methylene chloride phase from the water phase after each washing. The reaction product which remained dissolved in the methylene chloride phase was identified by infrared analysis to be a mixture predominately of tri(tridecyl)ammonium beta-octamolybdate with a small amount of tri(tridecyl)ammonium alpha-octamolybdate.

The tri(tridecyl)ammonium molybdates have been found to be a smoke retardant additive for vinyl chloride polymer compositions. When used as a smoke retardant additive, the tri(tridecyl)ammonium molybdates desirably are dissolved in an organic solvent for the molybdate (such as methylene chloride) and mixed with the dry vinyl chloride polymer particles. The methylene chloride then is allowed to evaporate from the vinyl chloride polymer leaving the tri(tridecyl)ammonium molybdate deposited on the vinyl chloride polymer particles. Preferably, from about 0.1 to about 20 parts by weight of a tri(tridecyl)ammonium molybdate is used per 100 parts by weight of vinyl chloride polymer.

Vinyl chloride polymers with which the tri(tridecyl)ammonium molybdates can be used as smoke retardant additives include homopolymers, copolymers and blends of homopolymers and/or copolymers, and include chlorinated polymers thereof. The vinyl chloride polymers may contain from 0 to 50 percent by weight of at least one other olefinically unsaturated monomer. Suitable monomers include 1-olefins containing from 2 to 12 carbon atoms such as ethylene, propylene, 1-butene, isobutylene, 1-hexene, 4-methyl-1-pentene, and the like; dienes containing from 4 to 10 carbon atoms, including conjugated dienes such as butadiene, isoprene, piperylene, and the like; ethylidene norbornene and dicyclopentadiene; vinyl esters and allyl esters such as vinyl acetate, vinyl chloroacetate, vinyl propionate, vinyl laurate, alkyl acetate, and the like; vinyl aromatics such as styrene, α-methyl styrene, chlorostyrene, vinyl toluene, vinyl naphthalene, and the like; vinyl allyl ethers and ketones such as vinyl methyl ether, allyl methyl ether, vinyl isobutyl ether, vinyl n-butyl ether, vinyl chloroethyl ether, methylvinyl ketone, and the like; vinyl nitriles such as acrylonitrile, methacrylonitrile, and the like; cyanoalkyl acrylates such as α-cyanomethyl acrylate, the α-β- and α-cyanopropyl acrylate, and the like; olefinically unsaturated acids and esters thereof including α,β-olefinically unsaturated acids and esters thereof such as methyl acrylate, ethyl acrylate, chloropropyl acrylate, butyl acrylate, hexyl acrylate, 2-ethylhexyl acrylate, dodecyl acrylate, octadecylacrylate, methoxyethyl acrylate, ethoxyethyl acrylate, hexylthioethyl acrylate, methyl methacrylate, ethyl methacrylate, butyl methacrylate, and the like.

The vinyl chloride polymer, in addition to the tri(tridecyl)ammonium molybdate, may contain the usual compounding ingredients known to the art such as fillers, stabilizers, opacifiers, lubricants, processing aids, impact modifiers, plasticizers, antioxidants, and the like.

Smoke retardancy may be measured using an NBS Smoke Chamber according to procedures described in ASTM E662-79 "Test For Specific Optical Density Of Smoke Generated By Solid Materials". Maximum smoke density (Dm) is a dimensionless number and has the advantage of representing a smoke density independent of chamber volume, specimen size or photometer path length, provided a consistent dimensional system is used. Percent smoke reduction is calculated using the equation:

$$\frac{Dm/g \text{ of control} - Dm/g \text{ of sample}}{Dm/g \text{ of control}} \times 100$$

The term "Dm/g" means maximum smoke density per gram of material. Dm and other aspects of the physical optics of light transmission through smoke are discussed fully in the ASTM publication.

The smoke retardant property of tri(tridecyl)ammonium molybdates is illustrated by the following examples:

EXAMPLES

The following recipe was used:

| Material | Parts by weight |
|---|---|
| Polyvinyl Chloride resin* | 100.0 |
| Lubricant** | 2.0 |
| Tin Stabilizer*** | 2.0 |
| Tri(tridecyl)ammonium molybdate | 5.0 |

*Homopolymer of vinyl chloride having an inherent viscosity of about 0.98–1.04; ASTM classification GO-5-15543.
**A commercial polyethylene powder lubricant (Microthene 510).
***Tin Thioglycolate 5.0 grams of the tri(tridecyl)ammonium hexamolybdate of Example I, dissolved in 230 milliliters of methylene chloride, were slowly added with constant stirring to 100 grams of the polyvinyl chloride resin in a porcelain dish heated in a water bath maintained at 40° C. Stirring was continued until the polyvinyl chloride resin appeared to be dry. The molybdate-polyvinyl chloride resin mixture was further dried in a vacuum oven at 40° C. for 28¾ hours. The lubricant and tin stabilizer of the recipe were added to the molybdate-polyvinyl chloride resin mixture and the resulting composition was milled on a two-roll mill for about 5 minutes at a roll temperature of about 165° C. The milled composition was pressed into a 6×6×0.050 inch sheet. Pressing was done at about 160° C. for 5 minutes using 40,000 pounds (about 14,900 Kg) of force applied to a 4-inch ram. The sample (Sample 1) received a 2 minute preheat before being pressed.

5.0 grams of the tri(tridecyl)ammonium molybdate mixture of Example II was mixed with other ingredients of the aforementioned recipe and formed into a 6×6×0.050 inch pressed sheet (Sample 2) as described above.

The molded samples were cut into 2⅞×2⅞×0.50 inch sections and tested against a control sample formed utilizing the aforesaid recipe but without use of the molybdate additive. Testing was performed using the flaming mode of the NBS Smoke Chamber Test (ASTM E662-79) described hereinabove. The test results are given in Table I.

TABLE I

| Sample | Dm/g* | Smoke Reduction (%) |
|---------|-------|---------------------|
| Control | 63.0  | —                   |
| 1       | 38.5  | 38.9                |
| 2       | 42.8  | 32.1                |

*Dm/g = maximum smoke density per gram of sample.

The improved smoke retardant vinyl chloride polymer compositions obtained by the inclusion of a tri(tridecyl)ammonium molybdate in the composition are useful wherever smoke reduction is a desirable property, such as in carpeting, house siding, plastic components for aircraft and passenger car interiors, and the like.

I claim:

1. Tri(tridecyl)ammonium molybdates having the empirical formula $$[(C_{13}H_{27})_3NH]_aMo_bO_c$$

where a, b and c are (2,6,19); (4,8,26) or (6,7,24).

2. The tri(tridecyl)ammonium molybdate of claim 1 wherein a is 2, b is 6 and c is 19.

3. The tri(tridecyl)ammonium molybdate of claim 1 wherein a is 4, b is 8, and c is 26.

4. The tri(tridecyl)ammonium molybdate of claim 1 wherein a is 6, b is 7, and c is 24.

* * * * *